United States Patent [19]

Peeters

[11] Patent Number: 4,476,306

[45] Date of Patent: Oct. 9, 1984

[54] METHOD OF PREPARING 2,4-DIHYDROXYPYRIMIDINE

[75] Inventor: Hermann Peeters, Niederkassel, Fed. Rep. of Germany

[73] Assignee: Dynamit Nobel AG, Cologne, Fed. Rep. of Germany

[21] Appl. No.: 401,294

[22] Filed: Jul. 23, 1982

[30] Foreign Application Priority Data

Jul. 23, 1981 [DE] Fed. Rep. of Germany ....... 3130455

[51] Int. Cl.³ ............................................ C07D 239/55
[52] U.S. Cl. .................................... 544/309; 544/314
[58] Field of Search .................................. 544/309, 314

[56] References Cited

U.S. PATENT DOCUMENTS 2,417,318  3/1947  Northey ............................. 544/309
3,718,649  2/1973  Dyer .................................. 544/309

Primary Examiner—Paul M. Coughlan, Jr.
Attorney, Agent, or Firm—Felfe & Lynch

[57] ABSTRACT 2,4-Dihydroxypyrimidine (uracil) is prepared from alkali formyl acetic acid ester by reaction with thiourea, heating with chloroacetic acid, and heating with acids.

17 Claims, No Drawings

METHOD OF PREPARING 2,4-DIHYDROXYPYRIMIDINE

This invention relates to the preparation of 2,4-dihydroxypyrimidine, also known as "uracil".

More specifically, the process involves the preparation of uracil from alkali formyl acetic esters in a four-step synthesis, without isolation of intermediate products, in accordance with the following scheme:

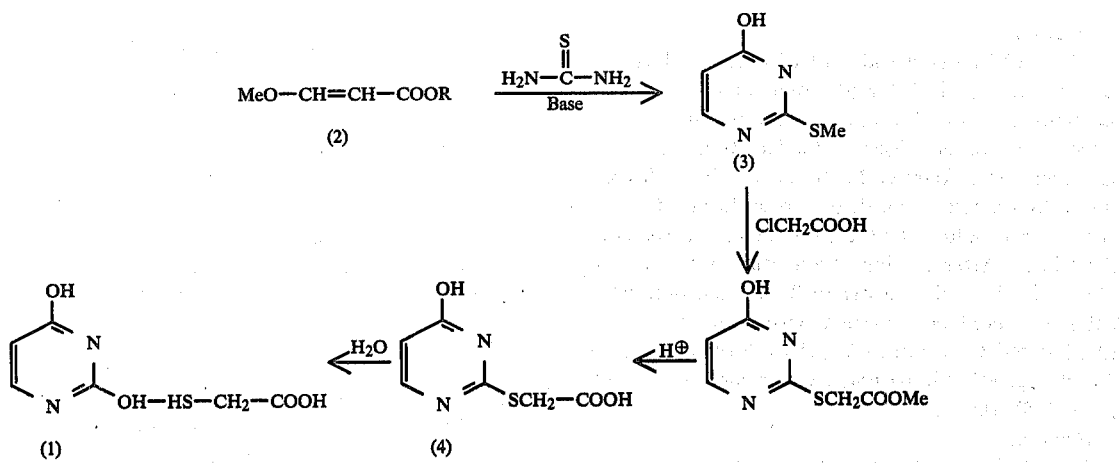

Uracil is a product that is widely used as an industrial chemical, in biochemistry, and in agricultural chemistry (Ind. Chem. Prod. Res. Dev., Vol. 17 No. 4 (1978)). 2-Carboxymethylthio-4-hydroxy-pyrimidine is a chemical intermediate that can be transformed to uracil or can serve as a starting product for a variety of pharmaceutically active pyrimidine derivatives.

Uracil can be made by a variety of methods. Low yields of about 55% are obtained by the reaction of malic acid with urea in the presence of 115% of oleum (J. Amer. Chem. Soc. 48 (1926) 2379). Large amounts of dilute sulfuric acid are produced and this is undesirable.

The preparation of uracil by heating 2-carboxymethylthio-4-hydroxypyrimidine with water, and by the reaction of 2-mercapto-4-hydroxypyrimidine with chloroacetic acid (Am. Chem. J. 40 (1908) 547) has already been described.

2-Carboxymethylthio-4-hydroxypyrimidine can be obtained in a 70% yield by the reaction of 2-mercapto-4-hydroxypyrimidine in aqueous alkaline medium with chloroacetic acid, followed by acidification (C. A. 52 (1958) 18702 h).

The synthesis of uracil and carboxymethylthiopyrimidine has been described, but only setting out from pure 2-mercapto-4-hydroxypyrimidine.

The problem therefore existed of finding a simple method for the preparation of uracil and of 2-carboxymethylthiopyrimidine, which, setting out from alkali formyl acetic acid alkyl esters, will lead directly to the end product without the isolation of intermediates, thereby achieving an appreciable technical advantage.

In has been found that this problem can be solved in a simple and elegant manner with a surprisingly high yield. Surprisingly, the by-products do not interfere with the reactions, and do not require the isolation of intermediates.

Accordingly, alkali formyl acetic acid alkyl ester is reacted first to the alkali salt of 4-mercapto-4-hydroxypyrimidine, for example in accordance with U.S. Pat. No. 3,718,649, and the latter is further reacted directly with chloroacetic acid.

For this purpose, for example, an alkali formyl acetic acid alkyl ester, in solid form or dissolved in polar solvents containing water, can be proportioned into an aqueous solution of alkali hydroxide and thiourea, preferably in water, at temperatures from about 10° to 25° C., and brought to reaction in the temperature range from 20° to 180° C. in approximately 1 to 2 hours. The amount of alkali hydroxide should be from 1 to 8 mol, preferably 2 to 5 mol, per mol of thiourea. The concentration of the reaction solution as regards thiourea should amount to from 0.2 to 6 mol/l, preferably 0.5 to 4 mol/l. The molar ratio of thiourea to alkali formyl acetic ester should be approximately 1:1.

In the alkali formyl acetic ester, Me can be an alkali metal, very preferably sodium or, less preferably, potassium, and alkyl can be a preferably saturated alkyl moiety of 1 to 8 carbon atoms, very preferably methyl or ethyl.

The reaction product is the alkali salt of 4-hydroxy-2-mercaptopyrimidine, which is easily soluble in water. This product is directly reacted with chloroacetic acid with cooling, at about 20° to 30° C., as described above. Further addition of alkali or water is unnecessary. The molar ratio of chloroacetic acid to the thiourea put in should be from 2:1 to 0.5 to 1, advantageously 1.5:1 to 0.75:1, or from 3 moles to 1 mole, preferably 1.5 moles to 1 mole, per mole of 4-hydroxy-2-mercaptopyrimidine alkali salt.

2-Carboxymethylthio-4-hydroxypyrimidine forms as salt, from the solution of which the free compound is precipitated by acidification with mineral acids such as sulfuric acid or hydrochloric acid or with chloroacetic acid, and adjustment to a pH of 7 or less, in some cases less than pH 3.

2-Carboxymethylthio-4-hydroxypyrimidine, in the presence of water—as precipitate in the precipitation water, for example—or while still moist in some cases, is further reacted to uracil.

It is also possible to isolate the substance in pure form after precipitation and dry it.

Uracil is obtained by adjusting the solution of the alkali salt of 2-carboxymethylthio-4-hydroxypyrimidine with acids, especially mineral acid such as sulfuric acid or hydrochloric acid, or with chloroacetic acid, to a pH of 7 or less, preferably of less than 3, and then heating at 50° to 200° C., advantageously at 100° C. From 1 to 30 equivalents, and very preferably 1 to 10 equivalents, of acid are used.

The reaction time amounts to from 1 to no more than 5 hours.

The uracil is produced in the form of a product insoluble in water, which is filtered out, washed with water and dried. The mercaptoacetic acid that is formed can be obtained by extraction of the mother liquor.

EXAMPLES

Example 1

12.0 g (0.3 mol) of sodium hydroxide is placed in 80 ml of water, and 15.2 g (0.2 mol) of thiourea and, in portions, 32.5 g (0.2 mol) of sodium formyl acetic acid ethyl ester (content 85%) is added at 20° C. The mixture is stirred for 2 hours at 20° to 25° C. Then 18.9 g (0.2 mol) chloroacetic acid, dissolved in 30 ml of water, is added with cooling at 20° C., and the mixture is refluxed for 1 hour. After cooling, the mixture is acidified with 10% sulfuric acid to a pH of 2, and the precipitating solid is filtered out, washed with water and vacuum dried at 50° C. Yield: 31.5 g (84.7% of the theory) of 2-carboxymethylthio-4-hydroxypyrimidine. Melting point 165°–168° C.

Example 2

30 g (0.75 mol) of sodium hydroxide is placed in 200 ml of water, and 380 g (0.5 mol) of thiourea and, in portions, 81.3 g (0.5 mol) of sodium formyl acetic acid ethyl ester (content 85%) are added at 20° C. The mixture is stirred for 2 hours at 20° to 25° C. Then 47.3 g (0.5 mol) of chloroacetic acid in 75 ml of water is added with cooling at 20° C. and the mixture is refluxed for 1 hour. After cooling, it is acidified with concentrated hydrochloric acid to a pH of 2 and refluxed for 3 hours. The solid is filtered off, washed with water and vacuum dried at 120° C. Yield: 47.7 g (85.2% of the theory) of 2,4-dihydroxypyrimidine (uracil). Melting point 338°–340° C.

It will be understood that the specification and examples are illustrative but not limitative of the present invention and that other embodiments within the spirit and scope of the invention will suggest themselves to those skilled in the art.

I claim:

1. Method of preparing 2,4-dihydroxypyrimidine of the formula

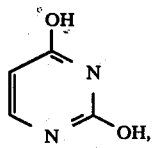

which process comprises reacting an alkali formyl acetic acid ester of the formula

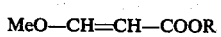

MeO—CH=CH—COOR (2), wherein

Me is an alkali metal and

R is an alkyl moiety with thiourea to form the alkali salt of 2-mercapto-4-hydroxypyrimidine of the formula

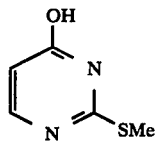

wherein

Me is defined as above and, without isolation of said 2-mercapto-4-hydroxypyrimidine, reacting the same with chloroacetic acid to form 2-carboxymethylthio-4-hydroxypyrimidine of the formula

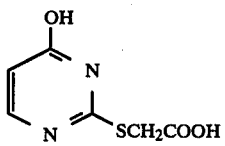

or the alkali salt thereof, and without isolation of the 2-carboxymethylthio-4-hydroxypyrimidine converting the same immediately to uracil, in the presence of water at a pH value of up to 7.

2. Process as claimed in claim 1, wherein Me is sodium or potassium.

3. Process as claimed in claim 1, wherein R is methyl or ethyl.

4. Process as claimed in claim 1, wherein the reaction is carried out in a polar solvent.

5. Process as claimed in claim 4, wherein said polar solvent contains water.

6. Process as claimed in claim 4, wherein said polar solvent is water.

7. Process as claimed in claim 1, wherein 1 to 8 equivalents of the base are used in the formation of 2-carboxymethylthio-4-hydroxypyrimidine.

8. Process as claimed in claim 7, wherein 1 to 3 moles of chloroacetic acid are used per mole of 4-hydroxy-2-mercaptopyrimidine alkali salt.

9. Process as claimed in claim 7, wherein 1 to 5 moles of chloroacetic acid are used per mole of 4-hydroxy-2-mercaptopyrimidine alkali salt.

10. Process as claimed in claim 1, wherein the reactions are carried out at temperatures from 20° to 180° C.

11. Process as claimed in claim 1, wherein the alkali salt of 2-carboxymethylthio-4-hydroxypyrimidine is first transformed to the free compound before conversion to uracil at a pH of up to 7.

12. Process as claimed in claim 1, wherein the conversion to uracil is carried out in the presence of an acid.

13. Process as claimed in claim 12, wherein said acid is at least one of hydrochloric acid, sulfuric acid and chloroacetic acid.

14. Process as claimed in claim 12, wherein 1 to 30 equivalents of said acid are used per equivalent of uracil formed.

15. Process as claimed in claim 12, wherein 1 to 10 equivalents of said acid are used per equivalent of uracil formed.

16. Process as claimed in claim 13, wherein the conversion to uracil is carried out at a reaction temperature of 50° to 200° C.

17. Process as claimed in claim 1, wherein the alkali salt of 2-carboxymethylthio-4-hydroxypyrimidine is transformed to the free compound by acidification at a pH up to 7.

* * * * *